United States Patent
Kilcher et al.

[19]

[11] Patent Number: 6,071,122

[45] Date of Patent: Jun. 6, 2000

[54] DENTAL INSTRUMENT AND METHOD FOR ITS MANUFACTURE

[75] Inventors: Beat Kilcher, Bosco Luganese; Beat A. von Weissenfluh, Gentilino, both of Switzerland

[73] Assignee: Hawe Neos Dental Dr. H. von Weissenfluh AG, Bioggio, Switzerland

[21] Appl. No.: 09/306,394

[22] Filed: May 6, 1999

[30] Foreign Application Priority Data

May 25, 1998 [CH] Switzerland ............................. 1145/98

[51] Int. Cl.⁷ ............................................... A61C 3/00
[52] U.S. Cl. ............................................. 433/141; 433/163
[58] Field of Search ................................. 433/141, 142, 433/143, 144, 163

[56] References Cited

U.S. PATENT DOCUMENTS

| | | | |
|---|---|---|---|
| 449,217 | 3/1891 | Good | 433/142 X |
| 883,592 | 3/1908 | Trigger | 433/141 X |
| 3,060,582 | 10/1962 | Kopp | 433/141 X |
| 4,690,642 | 9/1987 | Kyotani | 433/142 |
| 4,781,590 | 11/1988 | Weinstein | 433/142 |
| 4,919,616 | 4/1990 | Croll | 433/141 X |
| 5,267,854 | 12/1993 | Schmitt | 433/9 X |

*Primary Examiner*—Nicholas D. Lucchesi
*Attorney, Agent, or Firm*—Young & Thompson

[57] ABSTRACT

The adhesion of dental restorative materials, more particularly of composite materials containing an organic binder, to dental instruments can be reduced, essentially independently of the material of which the dental instrument is made, by providing the working surfaces with impressions. These impressions result in a reduction of the contact surface of the composite material on the working surface and thus in a reduction of the component of the adhesion which is due to physical attraction, e.g. to the van der Waals force. If the impressions are sufficiently small, a penetration of the composite material into the impressions is prevented by the high viscosity of the latter alone. If additionally the impressions are capable of being sealed by the tooth replacement material in contact therewith, an air cushion forms in the impressions which additionally counteracts a penetration of the tooth replacement material.

18 Claims, 5 Drawing Sheets

DENTAL INSTRUMENT AND METHOD FOR ITS MANUFACTURE

FIELD OF THE INVENTION

The present invention refers to a dental instrument, more particularly for applying and/or shaping tooth replacement materials, specifically composite materials, and to a method for its manufacture.

BACKGROUND OF THE INVENTION

Composite materials, i.e. tooth replacement materials containing binders in the form of hardenable, generally organic substances, are in the process of becoming the standard filling materials in dentistry. Therefore, the advantages and disadvantages of these materials acquire a central significance. An essential disadvantage is that up to now, all composite materials adhere more or less to the instrument which is used to apply or shape them. Thus, for example, the material has a stubborn tendency to be drawn off from the edges of the cavity. Since there is a trend to conform the composite materials as closely as possible to the final shape while they are still soft, in order to minimize the finishing work, this effect is becoming even more disturbing.

There have been numerous attempts to solve this problem. The most diverse materials have been used for the manufacture of instruments for composite materials, their surfaces have been treated, and many different shapes have been designed. Up to now, all these efforts have been unsuccessful.

The dentist mostly evades the difficulty by wetting the instruments with liquid composite bonding, thereby eluding the adhesion. As a result, however, the filling material is diluted and loses in quality. This is why this method is not recommended in science and research.

It will probably never be possible to eliminate the adhesion completely; neither would it be desirable. The composite material should adhere to the instrument to such a degree that a safe transport of the material from the dispensing location to the tooth is ensured without the risk that the portion falls off.

Some of the methods allowing to adjust the adhesion of the composite material on the instrument consist in coating the instruments with Teflon (C. M. Sturdevant, R. E. Barton, C. L. Sockwell, and W. D. Strickland (ed.), "The art and Science of Operative Dentistry", 2nd edition, C.V. Mosby Company, St. Louis, Toronto, Princeton, 1985, p. 365), wetting them with alcohol (J. Kanter, R. E. Koski, and J. E. Gough, The Journal of Prosthetic Dentistry 41 (1979), pp. 45–50), and in providing a titanium nitride surface coating (J. G. Steele, J. F. McCabe, and I. E. Barnes, J. Dent. 19 (1991), pp. 226–229). However, the application of separating agents (such as alcohol) requires an additional operation as well as the corresponding experience since the quantity of separating agent influences the adhesion and an excessive amount may alter the working properties of the composite material. If the instruments are manufactured from Teflon or coated with Teflon, the design of the surfaces and to a certain extent also the possible shapes are limited, on one hand, and the instruments are not always satisfactory in practice, on the other hand.

SUMMARY OF THE INVENTION

It is therefore an object of the present invention to provide a dental instrument whose adhesive properties with respect to composite materials are adjusted in a different manner.

This object is attained by a dental instrument wherein at least one working area of the surface of the dental instrument is covered with an array of impressions in order to reduce the adhesion of the tooth replacement material in said working area. The dependent claims describe preferred embodiments and manufacturing methods of the dental instrument.

The adhesion of composite materials to dental instruments is believed to be based on three main interactions, namely:

a) a mechanical one: The composite material penetrates into irregularities or recesses on the surface of the instrument and "interlocks" with the surface, so to speak. In the case of smooth surfaces, this interaction is of minor significance.

b) a physical one: Essentially, this adhesion is due to the forces of attraction between atoms of the instrument surface and of the composite material, i.e. by the van der Waals forces, amongst others. These forces increase with the contact surface and are especially significant in the case of smooth surfaces, i.e. particularly dental instruments, for example.

c) a chemical one: This adhesion would be created by a chemical bond between the instrument material and the composite material. Since the composite material and the dental instrument do not react with each other in any case, this interaction is generally insignificant.

The preceding shows that in practice, only the adhesive interactions a) and b) are significant. It is possible to adjust the adhesive properties of the dental instrument through the choice of a suitable material at least for the surface in contact with the composite material, and this possibility is indeed being used in practice, but it depends on the composition of the respective composite material. Generally, it is advantageous if the surface of the dental instrument consists of a material having a low surface tension. However, practice shows that tools provided e.g. with a Teflon surface are not suitable for all applications or rejected by practitioners for other reasons, on one hand, and that the desired adhesive properties are not always obtained, or not with all available composite materials, on the other hand.

Therefore, it is an object of the invention to propose a dental instrument providing improved adhesion characteristics with regard to dental composite materials.

According to the invention, however, the adhesion can also be adjusted by providing at least the working surface of a dental instrument with a discontinuous surface. Thus, essentially, the surface is provided with impressions, so that the composite material ideally only contacts the ridges between these impressions. In view of interaction a), however, it is preferably avoided that the composite material penetrates into the impressions, thus creating a mechanical adhesion. On one hand, this is prevented by making the impressions sufficiently small, so that the relatively consistent composite material can only hardly penetrate into the impressions. Particularly preferred, however, are impressions whose perimeter at the surface is closed and preferably does not substantially depart from the circular shape, in addition. Accordingly, the impressions may be hemispherical, for example. However, the horizontal cross-section of the impressions may also be approximately square or polygonal, preferably with rounded angles, while the other sections of the perimeter may be curved or irregularly shaped. The advantageous effect of the so designed impressions has been found in practice and is ascribed to the formation of a closed space or an air cushion in the impressions as they are closed by the composite material on the surface, thereby preventing the penetration of the composite material, particularly also under increased pressures which are produced when the composite material is shaped.

BRIEF DESCRIPTION OF THE DRAWINGS

The invention will be explained in more detail hereinafter with reference to the figures.

DETAILED DESCRIPTION OF THE INVENTION

Figure 1:
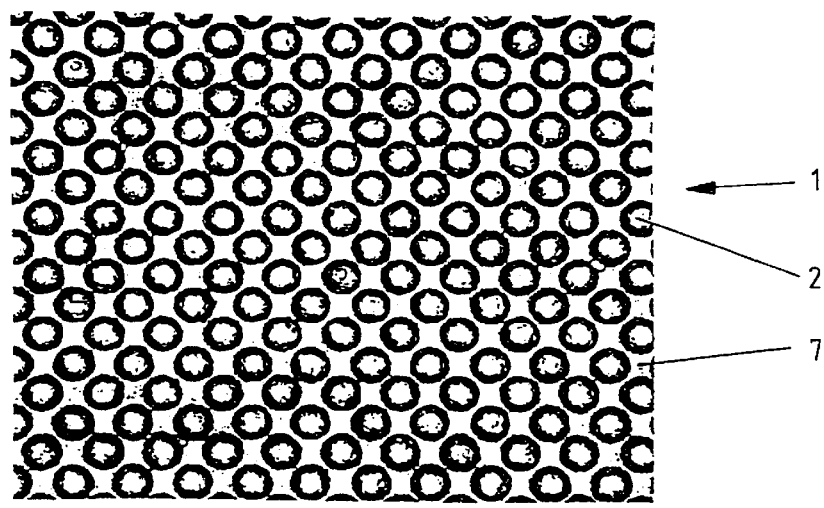
FIG. 1 shows a section of a surface provided with spherical micropits.

FIG. 1 shows a photograph of a surface 1 comprising a regular pattern of hemispherical micropits 2. According to FIG. 2, micropits 2 have an opening diameter 3 of 0.25 mm. The depth 4 of the micropits is about 0.1 mm.

Figure 3:
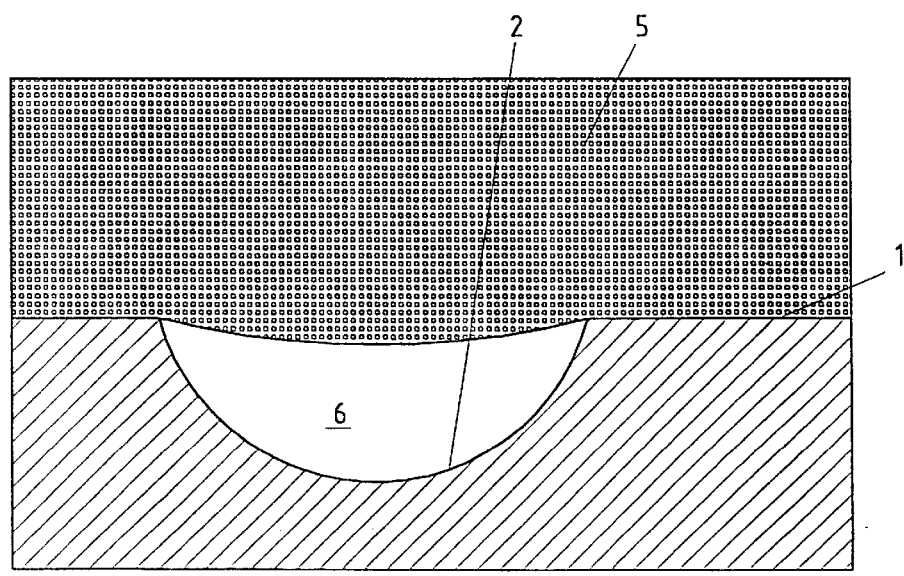
FIG. 3 schematically shows a perpendicular cross-section of an individual micropit.

FIG. 3 schematically shows the situation when surface 1 is covered with composite material 5. The composite material seals micropit 2, so that an air cushion 6 is formed therein. This air cushion 6 prevents a further penetration of composite material 5 into pit 2, which effect is furthered or reinforced by the high viscosity (e.g. in the range of 18 to 1400 Pa*s) of the currently used composite materials. Thus, since the composite material only contacts a part of surface 1, e.g. 50% in the present case, namely the remaining surface 7 between micropits 2, it is understood that the adhesion due to the physical interaction is significantly reduced.

Figure 4:
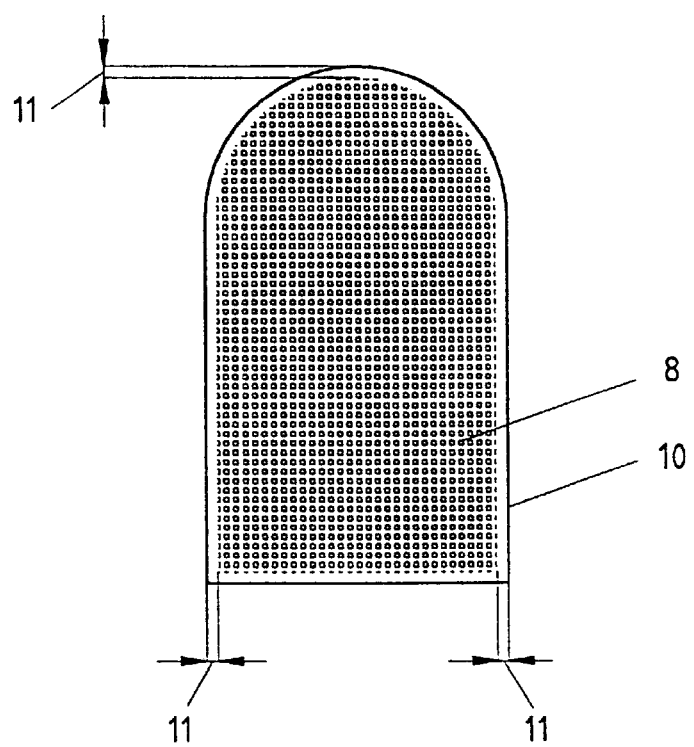
FIG. 4 shows a top view of a working surface of a dental instrument.

FIG. 4 shows an exemplary embodiment of a surface of a dental instrument according to the invention in a top view. In this case, surface 8 is almost completely covered with a regular array of micropits 9 (see enlarged illustration in FIG. 5). Practical tests have shown, however, that it is advantageous to leave a marginal zone 10 which is free of micropits. In the present case, this marginal zone has a width of 0.05 to 0.1 mm. This marginal zone allows to avoid that the edge of the dental instrument comprises incompletely formed micropits where the formation of an air cushion is impossible and into which the composite material might penetrate, thus leading to the formation of threads. The marginal zone also offers an increased resistance to wear.

The horizontal cross-section of the micropits is square with rounded angles. Edge length 12 amounts to 0.15 mm, and the distance 13 between two micropits 9 amounts to 0.05 mm. Such micropits are advantageously produced by a laser. The depth of micropits 9 amounts to approx. 0.05 mm. The angles of the square cross-section are rounded with a curvature radius 14 of 0.02 mm.

These approximately square pits were produced by means of a laser whose penetration depth was 0.05 mm.

Figure 6:
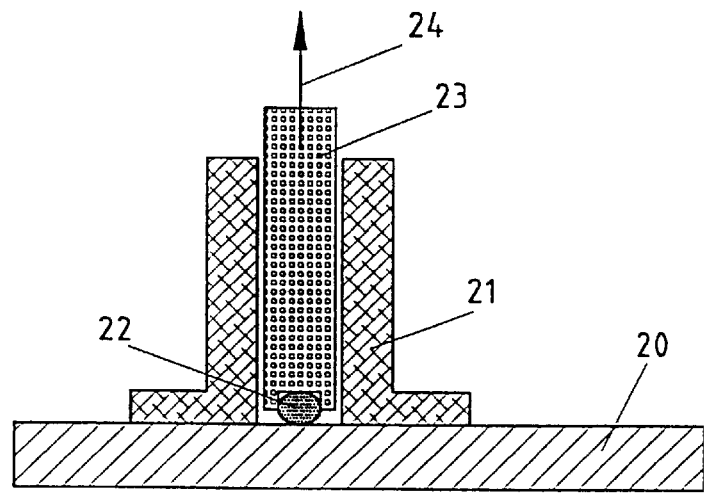
FIG. 6 shows a schematic cross-section of a measuring apparatus used in order to determine the adhesive force.

Comparative measurements of the two described examples of surface designs with respect to a smooth surface have been effected as follows. The basic material of the test pieces was steel. The adhesion was determined by means of an apparatus of which FIG. 6 shows a schematic cross-section.

Figure 2:
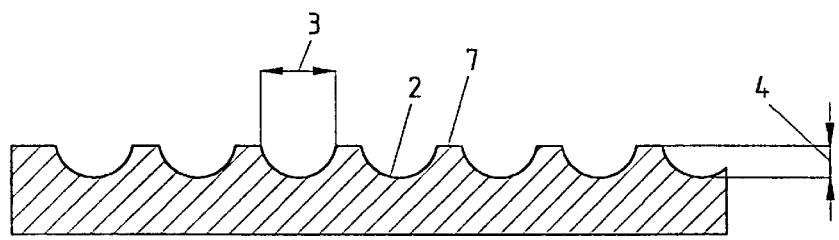
FIG. 2 shows a cross-section perpendicular to a surface according to FIG. 1, in principle.

A sleeve 21 is positioned on test piece 20. Inside sleeve 21, a predetermined quantity of composite material 22 is placed on test piece 20. This composite material is exposed during a determined time to the action of a gravity plunger 23 which fits into sleeve 21. Under its weight, the composite material 22 is pressed against surface 20. The adhesion is determined by measuring the force 24 which is required in order to pull out gravity plunger 23. The weight of the gravity plunger (in the present case, 35 g, i.e. 0.35 N) must be subtracted from the measured force. The results for the surface according to FIGS. 1 to 3 are listed in the following tables 1 and 2 (the untreated surface is steel having a roughness $R_a = 10^{-7}$ m).

TABLE 1

| Plunger action: 1 second | |
| --- | --- |
| Smooth surface | Micropits |
| 1.9 N | 0.8 N |
| 1.7 N | 0.5 N |
| 1.9 N | 0.9 N |
| 2.1 N | 0.6 N |
| 1.6 N | 0.8 N |

TABLE 2

| Plunger action: 5 seconds | |
| --- | --- |
| Smooth surface | Micropits |
| 5.2 N | 2.5 N |
| 6.2 N | 2.5 N |
| 6.0 N | 2.7 N |

Both tables show a reduction of the adhesion of about 50%, which approximately corresponds to the reduction of the contact surface of the composite material by the micropits, by the way. Furthermore, an examination of the surface after the adhesion tests showed that the composite material had not penetrated into the micropits.

Figure 5:
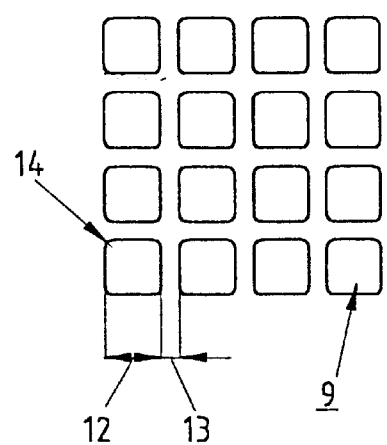
FIG. 5 schematically shows an enlarged detail of FIG. 4.

The results of adhesion measurements of the surface according to FIGS. 4 and 5 as compared to a smooth surface are shown in tables 3 and 4 (material of the test pieces: polybutylenterephtalate [PBT]).

TABLE 3

| Plunger action: 1 second | |
| --- | --- |
| Smoth surface (PBT) | Rounded square micropits (PBT; FIGS. 4 and 5) |
| 2.15 N | 0.75 N |
| 1.95 N | 0.65 N |

TABLE 3-continued

Plunger action: 1 second

| Smoth surface (PBT) | Rounded square micropits (PBT; FIGS. 4 and 5) |
|---|---|
| 1.85 N | 0.85 N |
| 2.35 N | 0.85 N |
| 2.35 N | 0.95 N |
| Mean value: 2.15 N | Mean value: 0.85 N |

TABLE 4

Plunger action: 5 seconds

| Smooth surface (PBT) | Rounded square micropits (PBT; FIGS. 4 and 5) |
|---|---|
| 3.35 N | 1.25 N |
| 3.95 N | 1.15 N |
| 4.35 N | 0.95 N |
| Mean value: 4.2 N | Mean value: 1.15 N |

In an optical measurement of the test piece surface provided with micropits, a surface proportion of the micropits of 61% was determined. According to table 3, a reduction of the adhesive force to approx. 39% of the adhesive force of the untreated surface is obtained, which corresponds exactly to the proportion of the surface left between the micropits in numerical terms. In the case of a longer plunger action according to table 4, the adhesion seems to be even further reduced, namely to 30% as compared to the smooth surface.

An exemplary embodiment of a practical dental instrument shall be explained herebelow with reference to FIGS. 7 to 13.

Figure 7:
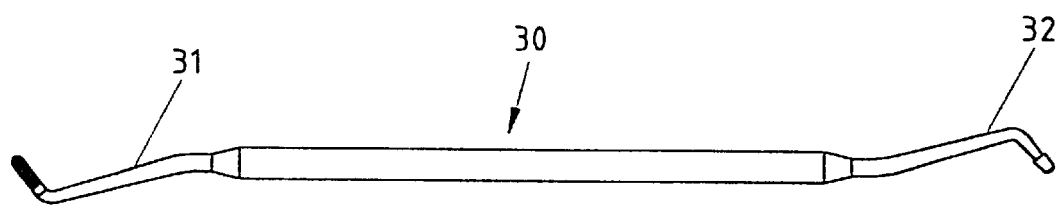
FIG. 7 shows an embodiment of a dental instrument comprising a plugger and a blade.
Figures 8, 9, 10:
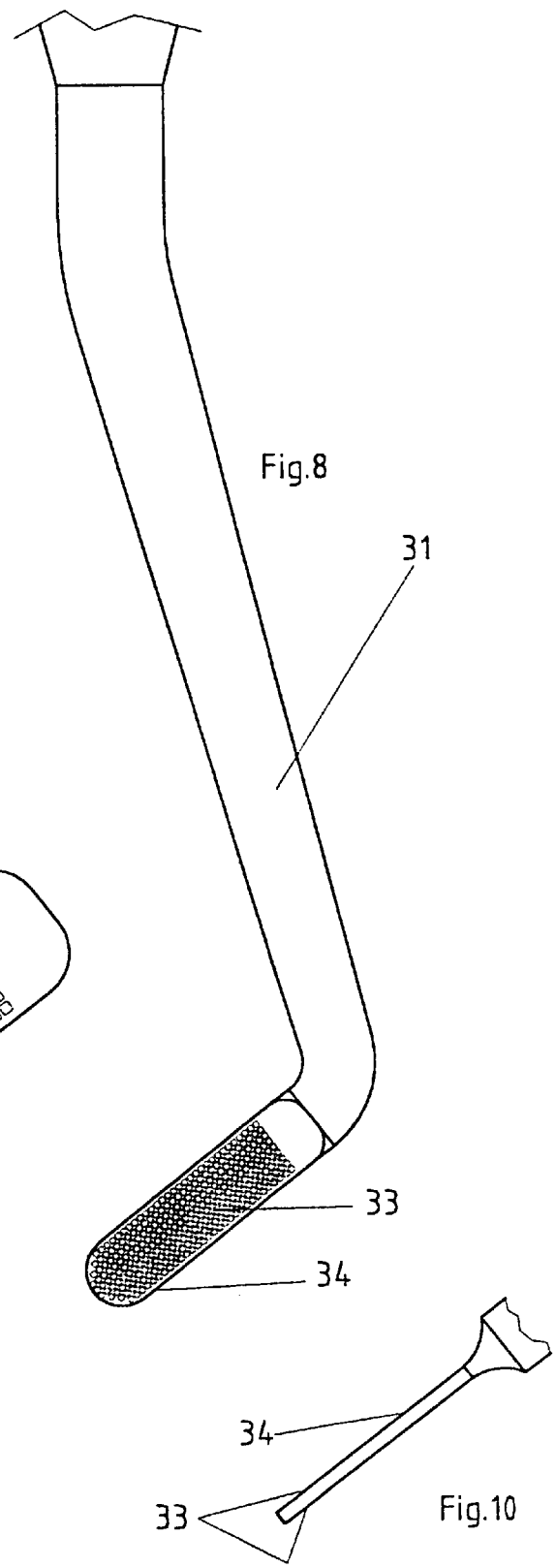
FIG. 8 shows the blade end of FIG. 7 on an enlarged scale.
FIG. 9 shows an enlarged top view of the working surface of the blade end of FIG. 8.
FIG. 10 shows a side view of the end of the tip of the blade end of FIG. 8.

One end 31 of dental instrument 30 is in the form of a blade while its other end 32 is in the form of a plugger (FIG. 7). Blade end 31 is shown on an enlarged scale in FIG. 8, FIG. 9 shows an enlarged top view of working surface 33, and FIG. 10 shows a side view of the tip of blade end 31. It will be noted that working surface 33 is provided on both sides of tip 34.

Figures 11, 12, 13:
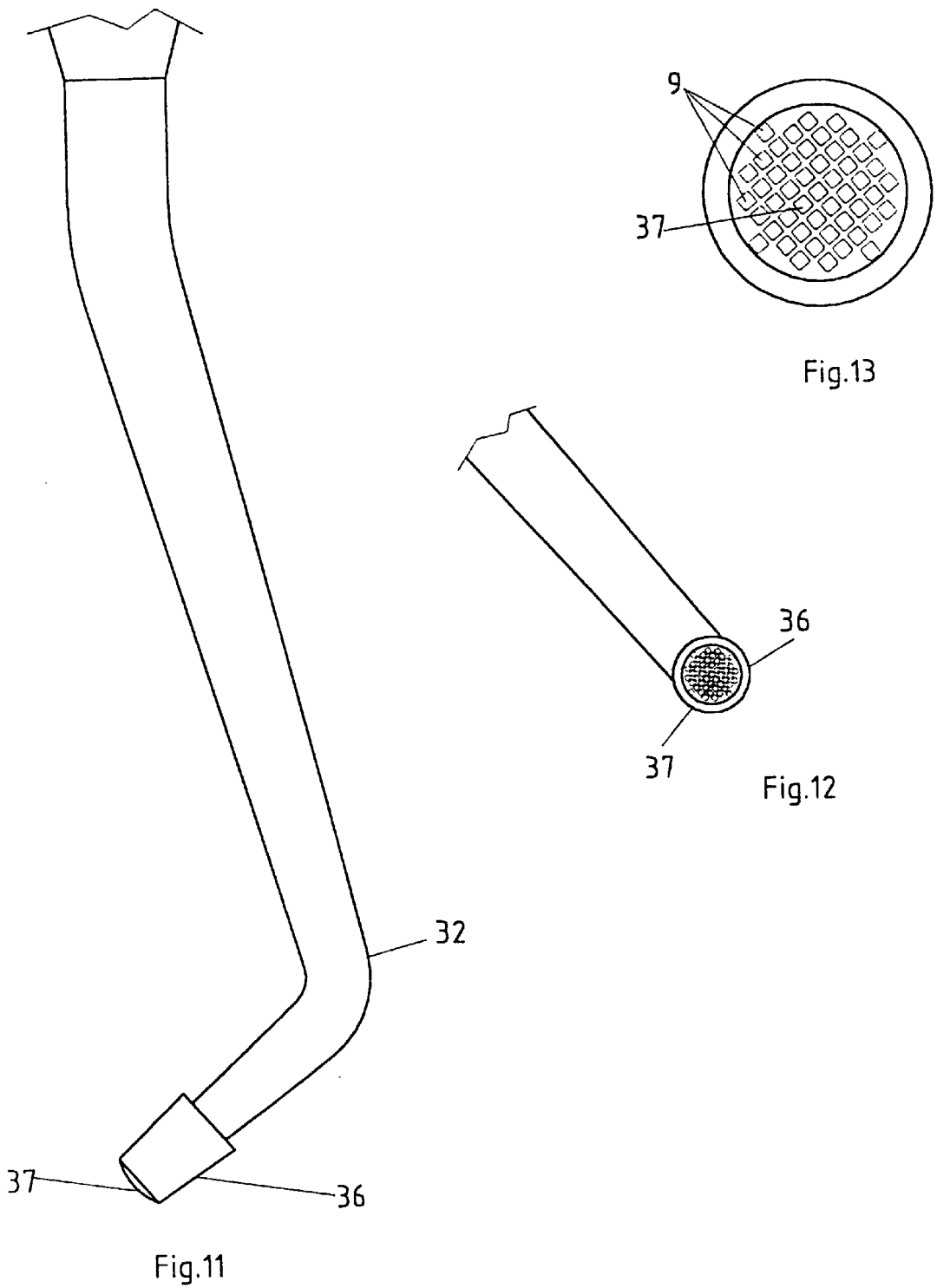
FIG. 11 shows the plugger end of the dental instrument of FIG. 7 on an enlarged scale.
FIG. 12 shows an enlarged top view of the tip of the plugger of FIG. 11.
FIG. 13 shows the working surface of the plugger of FIG. 11 on a further enlarged scale.

FIG. 11 shows an enlarged view of plugger end 32, whose tip 36 is provided with cambered plugger surface 37 provided with micropits (FIG. 12 shows a top view, and FIG. 13 an enlarged view of the working surface alone).

To those skilled in the art, a great number of variations of the surface structure of the invention are apparent from the preceding description. More particularly, the shape and the dimensions of the pits or, more generally, of the impressions in the surface may be varied according to further developments of the machining techniques, in particular, and of the properties of the composite materials, particularly their viscosity. In particular, the described simple cross-sections (i.e. square with rounded angles, as a result of the diameter of the laser beam; or spherical) shall be construed as mere examples, while other shapes such as elliptical, oval, or polygonal shapes with 5, 6 or more angles are possible. It is also conceivable that the pits have different shapes, e.g. partly circular, partly polygonal, and partly triangular.

In view of the formation of an air cushion which effectively prevents the penetration of the composite material, it is advantageous if the majority of the impressions are so designed that the composite material seals the impressions in a substantially air-tight manner. The shape of the cross-section of the pits perpendicularly to the surface may be varied in a wide range as well. However, in view of the air cushion, it is quite obvious that the space should not be too large, i.e. the pits should not be too deep in order to ensure that a slight penetration of the composite material already results in a high pressure increase within the air cushion. On the other hand, if the pits are too shallow, the composite material might again touch the bottom of the micropits. However, the optimum geometry and the dimensions of the micropits can be determined in simple experiments, possibly combined with adhesion measurements, which can easily be performed by those skilled in the art on the basis of the description of the present invention.

Generally speaking, a reduction of the remaining surface 7 leads to an improvement, i.e. to a reduction of the adhesion, since the contact surface and thus the relevant surface for the physical adhesion is reduced. A lower limit for the proportion of micropits within the total surface is believed to be 30% (equivalent to 70% of remaining surface 7); a proportion of 50%, as indicated in the examples, is easily obtained, while 70% are possible as well. A further increase of the percentage, e.g. in the course of further developments in the manufacturing techniques, can be expected.

Injection molding has been found to be an economical alternative production method as the micropits can be manufactured simultaneously by means of a mold having the corresponding negative shape.

What is claimed is:

1. In a dental instrument having at least one working area for applying and shaping a tooth replacement composite material, the improvement wherein:

the working area comprises the discontinuous surface;

said discontinuous surface including an array of micropits having surface openings and being structured and arranged to reduce adhesion of the tooth replacement composite material in said micropits when said tooth replacement composite material is applied to said working area.

2. The dental instrument of claim 1, wherein the surface openings of at least a majority of said micropits form a closed perimeter, said micropits being structured and arranged to be sealed in a substantially air-tight manner by the tooth replacement composite material when applied to said working area, thereby forming an air cushion in said micropits which counteracts penetration of the tooth replacement composite material into said micropits.

3. The dental instrument of claim 1, wherein said micropits constitute at least 30% of the surface of said working area.

4. The dental instrument of claim 3, wherein said micropits constitute at least 50 percent of the surface of said working area.

5. The dental instrument of claim 4, wherein said micropits constitute at least 70 percent of the surface of said working area.

6. The dental instrument of claim 1, wherein the depth of at least a majority of said micropits is equal to $1/10$ of the mean diameter of their surface openings.

7. The dental instrument of claim 6, wherein the depth of at least a majority of said micropits is equal to at least $1/4$ of the mean diameter of their surface openings.

8. The dental instrument of claim 7, wherein the depth of at least a majority of said micropits is equal to at least $1/3$ of the mean diameter of their surface openings.

9. The dental instrument of claim 1, wherein the mean diameter of the surface openings of said micropits is smaller than 1 mm.

10. The dental instrument of claim 9, wherein the mean diameter of the surface openings of said micropits is smaller than or equal to 0.5 mm.

11. The dental instrument of claim 10, wherein the mean diameter of the surface openings of said micropits is smaller than or equal to 0.2 mm.

12. The dental instrument of claim 1, wherein at least in the area of their surface openings, a majority of said micropits are rotation-symmetrical.

13. The dental instrument of claim 1, wherein at least in the area of their surface openings, a majority of said micropits essentially have contours of one of the following shapes: polygonal, circular, elliptical and oval.

14. The dental instrument of claim 13, wherein at least in the area of the surface openings, a majority of said micropits essentially have contours with three to ten angles and straight or curved edges.

15. The dental instrument of claim 1, wherein at least a substantial portion of said working area is surrounded by a zone which is free of micropits, and whose width is equal to at least 1/10 of the mean diameter of the surface openings of at least a majority of said micropits.

16. The dental instrument of claim 15, wherein at least a substantial portion of said working area is surrounded by a zone which is free of micropits, and whose width is equal to at least 1/4 of the mean diameter of the surface openings of at least a majority of said micropits.

17. A method for manufacturing a dental instrument having at least one working area for applying and shaping a tooth replacement composite material, the working area comprising a discontinuous surface including an array of micropits having surface openings and being structured and arranged to reduce adhesion of the tooth replacement composite material in said micropits when said tooth replacement composite material is applied to said working area, wherein said micropits are obtained through excavation by a laser.

18. The method according to claim 17, wherein the working area is produced by injection-molding.

* * * * *